(12) United States Patent
Noel

(10) Patent No.: US 11,331,192 B2
(45) Date of Patent: May 17, 2022

(54) FRICTIONLESS HIP JOINT

(71) Applicant: Hector Noel, Miami, FL (US)

(72) Inventor: Hector Noel, Miami, FL (US)

(73) Assignee: NOEL RAELS ORTHO DEVICES INCORPORATED, Port Saint Lucie, FL (US)

( * ) Notice: Subject to any disclaimer, the term of this patent is extended or adjusted under 35 U.S.C. 154(b) by 0 days.

(21) Appl. No.: 16/828,594

(22) Filed: Mar. 24, 2020

(65) Prior Publication Data

US 2020/0222197 A1 Jul. 16, 2020

Related U.S. Application Data

(63) Continuation-in-part of application No. 15/829,267, filed on Dec. 1, 2017, now Pat. No. 10,596,005.

(60) Provisional application No. 62/491,829, filed on Apr. 28, 2017.

(51) Int. Cl.
*A61F 2/36* (2006.01)
*A61F 2/34* (2006.01)
*A61L 27/36* (2006.01)

(52) U.S. Cl.
CPC ............. *A61F 2/3609* (2013.01); *A61F 2/34* (2013.01); *A61L 27/36* (2013.01); *A61F 2002/3483* (2013.01); *A61F 2002/365* (2013.01); *A61F 2002/3615* (2013.01); *A61F 2250/0069* (2013.01); *A61F 2310/00047* (2013.01); *A61F 2310/00389* (2013.01)

(58) Field of Classification Search
CPC ................ A61F 2/3601; A61F 2/3609; A61F 2002/2828; A61F 2002/3611; A61F 2002/3625; A61F 2002/365; A61F 2002/3652; A61F 2002/30474; A61F 2002/30479; A61F 2002/30495; A61F 2002/30639; A61F 2002/3064; A61F 2002/30644; A61F 2002/30645; A61F 2002/30563; A61F 2002/30583; A61F 2002/30673; A61F 2002/3635; A61F 2002/3641; A61F 2002/3619; A61F 2002/3645

See application file for complete search history.

(56) References Cited

U.S. PATENT DOCUMENTS

| | | | |
|---|---|---|---|
| 2,362,975 | A | 11/1944 | Comb |
| 4,770,658 | A | 9/1988 | Geremakis |
| 4,842,605 | A | 6/1989 | Sonnerat et al. |
| 5,556,434 | A | 9/1996 | Epstein et al. |

(Continued)

FOREIGN PATENT DOCUMENTS

| | | | | |
|---|---|---|---|---|
| EP | 0524857 A1 | * | 1/1993 | ............ F16C 19/381 |
| FR | 2261743 | | 9/1978 | |

(Continued)

*Primary Examiner* — Javier G Blanco
(74) *Attorney, Agent, or Firm* — Malloy & Malloy, PL; Jennie S. Malloy; Peter A. Matos

(57) ABSTRACT

An orthopedic prosthesis includes a head which internally accommodates the major motion of a patient, e.g., during walking, thereby reducing wear against a cup or liner. A neck may be utilized which rotates within the distal member about an axis aligned with the major motion of the patient. The orthopedic prosthesis may also include a sacrificial anode, a seal made of natural fibers, and utilize lubricant made of honey.

11 Claims, 6 Drawing Sheets

(56) References Cited

U.S. PATENT DOCUMENTS

| | | | |
|---|---|---|---|
| 5,725,377 | A | 3/1998 | Lemler et al. |
| 5,725,597 | A | 3/1998 | Hwang |
| 5,800,558 | A | 9/1998 | LaHaise, Sr. |
| 5,888,211 | A | 3/1999 | Sanders |
| 6,328,764 | B1 | 12/2001 | Mady |
| 6,336,941 | B1 | 1/2002 | Subba Rao et al. |
| 7,425,214 | B1 | 9/2008 | McCarthy et al. |
| 8,034,116 | B2 | 10/2011 | Vander Meulen et al. |
| 8,702,802 | B2 | 4/2014 | Linares et al. |
| 8,702,804 | B2 | 4/2014 | Smith et al. |
| 8,974,540 | B2 | 3/2015 | Podolsky |
| 9,326,862 | B2 | 5/2016 | Smith et al. |
| 10,596,005 | B2 | 3/2020 | Noel |
| 2006/0271200 | A1 | 11/2006 | Greenlee |
| 2011/0263528 | A1 | 10/2011 | Keiji et al. |
| 2017/0000996 | A1* | 1/2017 | odonnell .............. A61N 1/0529 |
| 2019/0046488 | A1 | 2/2019 | Rosenblatt et al. |

FOREIGN PATENT DOCUMENTS

| | | |
|---|---|---|
| WO | WO2018201026 | 1/2018 |
| WO | WO2021195082 | 9/2021 |

\* cited by examiner

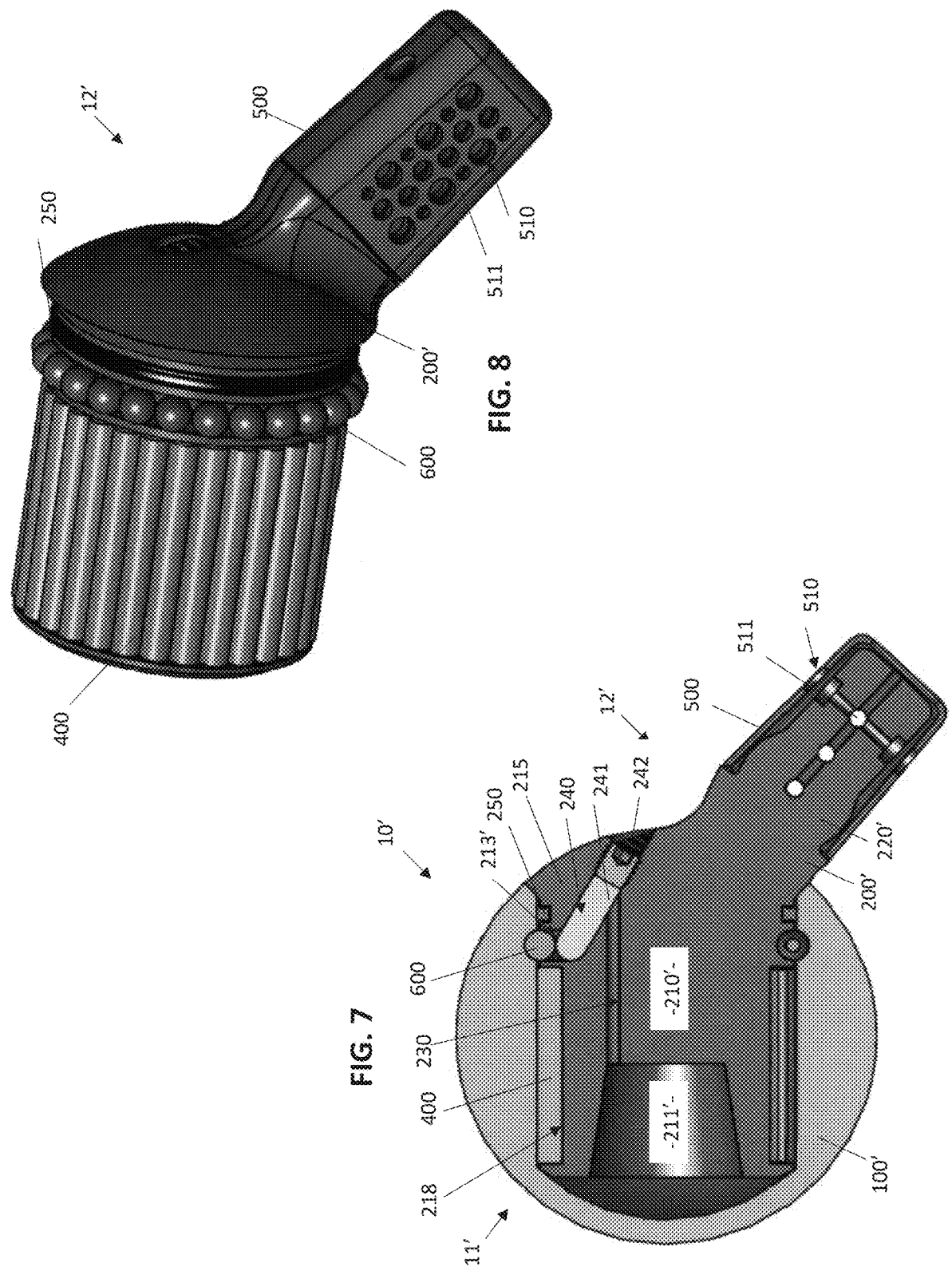

FRICTIONLESS HIP JOINT

CLAIM OF PRIORITY

The present non-provisional patent application is a continuation-in-part application of a currently pending and prior filed non-provisional patent application having Ser. No. 15/829,267 filed on Dec. 1, 2017, and which claims priority pursuant to 35 U.S.C. Section 119(e) to a provisional patent application having Ser. No. 62/491,829 filed on Apr. 28, 2017, the contents of which are incorporated herein by reference in its entirety.

BACKGROUND OF THE INVENTION

Field of the Invention

The present invention is directed to an improved orthopedic hip prosthesis as well as several advancements in the art including the use of naturally occurring, bio-compatible lubricants, seals made of natural fibers, and the use of a sacrificial anode.

Preliminary Statement of the Invention

This device was designed to, among other things, simultaneously:
1) Significantly reduce the current incidents of hip dislocations and the medical care that follows;
2) Eliminate the need for hip revision surgery;
3) Confine metallic wear particles away from body tissue reducing the potential for metal poisoning to an insignificant threat;
4) Increase the ability to support substantially greater weights without component damage from friction;
5) Have constant and proper lubrication; and
6) Increase or maintain a large range of motion.

A brief statement of how the foregoing is accomplished, without limiting the scope of the invention, follows:

Hip dislocations following hip replacement surgery have a direct relationship to the size of the femur ball head used. It was believed that smaller ball heads produce less friction within the liner, but unfortunately a small size ball head tends to dislocate somewhat easily. It was later discovered that larger ball heads dislocated less often but increased the surface finish damage from friction, and therefore a direct relationship to size has been established. That is, a larger the ball head develops more wear on the liner because of the greater circumference and speed of the ball head moving against the liner. Current ball head sizes are a compromise between friction damage, the patient's anatomy, and desired range of motion.

In revision surgery, the ceramic liner that is mounted within the pelvis and receives the ball head is worn out from, among other causes, "edge loading". Both liner and ball head are replaced and the mating parts have a useful life of 10-20 years depending on activity. However, liners eventually break down as they rely only on the body's fluids which are an insufficient lubricant to protect against that type of edge load and wear.

Removing this ceramic liner altogether can not only eliminate revision surgery regarding liner replacement but allow a larger ball head (up to 2.125") to occupy that now vacated space leading to significantly reduced hip dislocations while maintaining a large range of motion.

By moving the friction interaction that occurs between the ball head and ceramic liner so as to now happen within the mechanism of the ball head itself, the invention compartmentalizes any metallic wear particles so that they are contained safely and will avoid contaminating the body. A properly and/or continuously lubricated, precision bearing can withstand greater loads before breaking down as opposed to the relatively dry metal or ceramic ball riding in a metal or ceramic socket. The present invention contemplates containing a built-in lubrication reservoir that, once filled, should outlive the patient. In one embodiment, the desired lubricant may comprise tallow, a processed animal or human fat that melts from solid to viscous between 85° f and 104° f, which is conveniently the temperature range of humans as well. However, other lubricants may still be used.

Description of the Related Art

The modern hip implant, while a significant technological advancement, still suffers from several deficiencies that cause complications in its use, lead to revision surgery, or make it vulnerable to post-operative dislocation, among other issues. The present invention addresses several deficiencies, while improving the life span of a hip implant, all while providing a familiar silhouette, such that surgical techniques need not be modified much, if at all.

A typical hip implant procedure requires removal of a substantial portion of the femur bone, as well as preparation of the acetabulum with a "shell" or "cup" to receive the new prosthetic. The term "cup" as used herein, may comprise a multi-component assembly including at least a shell and a liner. In general, however, the head and neck of the femur is removed and a portion of the remaining femur is hollowed out. The femur stem of a hip prosthesis is inserted into the hollow portions of the femur, the hip prosthesis having a neck and head protruding from the femur, loosely approximating the patient's anatomical femur neck and head. The acetabulum is prepared via a reaming process to create a socket into which a shell or cup is inserted. The cup may consist of two pieces, a shell and a liner. The shell is generally made from metal and is seated into the reamed acetabulum. The liner, which may be made of ceramic or a desired polymer, is seated into the shell and the head of the prosthesis is seated into the liner. The shell, as well as the stem, are rigidly secured to the patient's existing bone structure. They may be cemented into place or be seated with an interference fit, e.g., by hammering into place. They may also include a particular surface treatment, such as to increase porosity, such that over time, the patient's bone and/or tissue will naturally fuse with the shell and stem.

As may be expected, wear is of particular concern. Over the lifetime of a patient, the head may be expected to undergo innumerable rotations and gyrations within the liner, and a substantial portion of those may be expected to occur under loading, such as when the patient is standing, walking, running, jumping, carrying an object, etc. The weight of an obese patient can significantly accelerate wear due to increased friction. Thus, reduction of friction between the wear surfaces has been a significant focus within a primary field of tribology and the study of material selection for friction, lubrication, and wear characteristics. Liners are generally selected of suitable metal or polymers, such as high-density polyethylene ("HDPE") or ultra-high-molecular-weight polyethylene ("UHMWPE"). The femoral head is generally selected of a hard, brittle material, such as cobalt chromium or ceramic, which is then polished, to further reduce wear of the liner. Suitable combinations of materials between the liner and the head, such as metal-on-polymer, ceramic-on-ceramic, or metal-on-metal, may have different advantages or disadvantages, to be considered by medical professionals.

In this context, certain disadvantages become apparent. Initially, given the space constraints within the acetabular region of a patient, the size and/or thickness of the shell and liner serves to limit the overall size of the implant. Therefore, inclusion of a liner serves to reduce the size of the femoral head that may be used and, if sufficient force is applied, the femoral head can be leveraged out of the cup/liner. Though a larger femoral head may decrease the risk of dislocation, because the femoral head may rotate further within the socket before impingement of the neck occurs on the liner, as compared to a femoral head of smaller diameter, a larger femoral head will also lead to increased volumetric wear from increased inertial forces. However, the limiting factor in determining the size of the femoral head is the thickness of the liner. Accordingly, there is a need in the art for an improved prosthesis which allows a larger femoral head to be utilized.

Yet another disadvantage present in current hip implants stems from the use of increasingly hard and highly brittle materials, a trait thought to be desirable as harder materials can be polished to provide lower friction. However, a common failure mode in hip implants is a fracture leading to catastrophic structural failures in the implant, especially around the neck and femur shank. In considering that the femoral head is offset by the neck from the femur shank, it is apparent that stresses transferred through the femur shank into the hip will cause a moment, or a torque, about the neck and/or femur shank. The repeated stresses transferred through the shank over the lifetime of the patient, coupled with the neck-stem leverage or bending moment, may result in micro-motion and, due to the brittleness of the materials, fatigue will lead to crack propagation and eventually failure of the prosthesis. Such micro-motions are a more significant problem for modular implants, where the head is formed of a separate component from the neck and is press-fit onto the neck via a taper, which can be worked loose.

Yet another deficiency apparent in the modern hip implant is corrosion. In one respect, modular hip implants, such as those with separate head and neck portions, were introduced to simplify revision surgery, by offering the ability to simply replace the head, and also allows the use of different materials where desired, such as a ceramic head, which cannot be integrally formed with a metal neck. Alternatively, cobalt-chrome heads are selected for the material's hardness, which is ideal for use as a bearing surface, especially when polished. However, the rigidity, or modulus of elasticity, of cobalt-chrome is significantly higher than that of bone, which makes it unsuitable for use as a femoral stem, as it would transfer significant stresses into the bone. Hence, titanium alloys are generally selected as femoral stem components. The use of multiple metals for their desirable material traits, however, leads to corrosion, especially at the interface of both the head-to-neck taper, and the neck-to-stem taper where the modular unit is mounted to a femoral stem.

Mechanical corrosion, such as crevice corrosion or fretting is a common mode. Crevice corrosion may occur at the interface of two materials and, in the context of orthopedic implants, can be caused by the breakdown of surface oxide layers on the prosthesis, which otherwise serve to protect the materials from the electrochemical and saline environment of a patient's body. Fretting is the mechanical assistance of crevice corrosion, due to a number of factors, including the repeated stresses applied at the neck due to the leveraging of the patient's weight through the offset stem. As can be appreciated, the more modularity in an implant, such as those with both modular heads and necks, the more chance for debris to form due to corrosion at the modular interfaces.

The inventor herein considers that another mode of this corrosion is galvanic corrosion. Specifically, when dissimilar metals are disposed in an electrolyte solution, such as when a cobalt chromium head is press fit onto a titanium femur shank and disposed within the corrosive saline environment of a patient's body, an electrochemical cell is created. One metal serves as an anode, while the other metal serves as a cathode, and corrosion at the anode is accelerated due to the difference in electrical potential.

This effect may be amplified by the piezoelectric properties of bone, and the cyclical pressures created at the tapers, generating further voltage when stressed. In particular, when a patient loads the femur, such as when walking, an electromotive force is generated within the femur, thereby causing voltage to flow. This voltage may follow a path through the implant and into the shell and pelvis. When combined with a dissimilar metal implant acting as a cathode/anode, galvanic corrosion can be accelerated. Moreover, or alternatively, the triboelectric effect may cause a buildup of charged particles due to the constant rubbing of the ball against a dissimilar liner, further contributing to an electrical potential generated across the implant.

This galvanic corrosion, acting in concert with mechanical corrosion, as well as the cyclical loading causing fatigue within the implant, leads to significant failure rates and additional complications.

With the foregoing in mind, there is a need in the field of art relating to hip replacements for an improved device which provides for the use of a larger femoral head, thereby reducing the occurrence of dislocation. Such a device also reduces the wear on the femoral head by transferring the majority of motion of the prosthesis away from the acetabular interface and thereby allows for selection of materials which are more durable, and do not cause corrosion from dissimilar metals. Additionally, the present invention provides for greater range of motion, eliminates unwanted noises caused by wear, is capable of carrying tremendous loads without wear, and is self-lubricating.

Further advancements in the art, which are disclosed herein, include the use of a sacrificial anode to assist in corrosion resistance of critical components, the use of naturally occurring, bio-compatible lubricants, and seals made of natural fibers. As is presently understood, galvanic corrosion is one of the mechanisms which virtually any metallic implant must undergo. While, the use of a sacrificial anode can preserve the critical components of an implant, the selection and placement of such a sacrificial anode must be carefully attended, otherwise the sacrificial anode will release metallic ions and other debris into the body. The present invention discloses at least one arrangement for the deployment of a sacrificial anode within an implant such that all metallic ions and particles are trapped within the implant itself, and not released into the body.

These and other problems present in the art are addressed in the following embodiments of the present invention.

SUMMARY OF THE INVENTION

The present invention is directed to an orthopedic hip prosthesis ("hip implant") to be implanted within a patient that addresses several needs in the field of art relating to hip replacement. One advantage of the present invention is the elimination of the traditional liner, which is generally quite thick. Removing the liner (or in certain embodiments, significantly reducing the liner's thickness) allows for the use of a larger diameter head than would otherwise be suitable, given the space constraints in the acetabular region. As is known, a larger head leads to larger volumetric wear, especially considering that in the absence of a liner, the head will rotate against the shell. In order to address the increased volumetric wear, one embodiment of the present invention proposes to internalize much of the repetitive, cyclical, rotation of the implant within the head. Alternatively, a substantially thinner liner than heretofore considered suitable may be utilized in conjunction with the present invention.

In general principle, the present invention recognizes that the major axis of motion in a hip joint is that which provides rotation during walking and running movements. While a hip joint provides for other motion, e.g., laterally, these motions are minor in comparison. Accordingly, one aspect of the present invention internalizes at least the major motion interiorly of the orthopedic prosthesis, thereby significantly reducing the wear that otherwise occurs between the head and liner of an ordinary implant, eventually causing such complications as tissue necrosis or pseudo-tumors.

In at least one embodiment, the present invention is directed to a coaxial, fully articulating joint, which is particularly suitable as an orthopedic hip prosthesis, in which the head includes at least two portions, a proximal member and a distal member. The proximal member is dimensioned and configured to be received directly by the acetabulum, or if not directly, then preferably at least by a thin shell installed within the acetabulum. Such a "thin shell" as may be utilized by certain embodiments of the present invention functionally replaces both the shell and liner of the prior art. The proximal member is disposed in substantially unrestricted relation within the acetabulum in that it is free to rotate within the acetabulum or liner, such that minor motions of the patient's leg, e.g., lateral motions, can be accommodated when desired.

The distal member is dimensioned and configured to be fixedly connected to a femur of the patient. The distal member may include a shank that is either directly installed within a femur of the patient or may be coupled to a more traditional femur stem, which is in turn installed within the patient's femur. The proximal member and distal member are correspondingly dimensioned and configured to be adjoined at a mating interface, which may be internally of the proximal member, but which constrains movement of the distal member within the proximal member to rotation about a single axis, i.e. a single degree of freedom of movement relative to the proximal member. Preferably, this single degree of freedom of movement is coaxial, when properly implanted within a patient (or installed in a walking mechanism of, e.g., a robot), with the patient's natural axis of rotation of the legs during walking and running motions. Stated otherwise, the distal member may rotate within the proximal member about an axis that can be aligned with the patient's natural axis of rotation of the legs. Accordingly, the major motion of the patient is accommodated interiorly of the orthopedic prosthesis, and does not require any movement of the head within the acetabulum during such major motions.

In yet another embodiment, the proximal member comprises a head that includes a recess, while one embodiment of the distal member comprises a neck that includes an axle. The axle may be rotationally disposed within the recess of the head. The axle and the head are correspondingly dimensioned and configured such that the invention may be implanted with at least the majority of the rotational axis of the axle aligned with the natural walking axis of the patient. Accordingly, movement of the implant due to, e.g., walking or running, causes a rotation of the axle within the head, while movement of the head relative to the shell is minimized, if not entirely eliminated. Movement of the head relative to the shell is therefore only required during off-axis and/or low-loading movements, such as lateral motions of the patient's leg, e.g., when putting on footwear.

Given that the majority of rotational movement is internalized within the head, the mating surfaces between the axle and recess may be lubricated and such lubrication will be maintained within the head, rather than spreading to other parts of the patient's body. Accordingly, wear is significantly reduced, perhaps extending the life of the implant of the present invention to even longer than that of a patient. An additional advantage is that if debris is generated, it will be retained inside the head, and thereby avoid complications for patients where, e.g., metal, ceramic, or polyethylene chips or filings are released into the patient's surrounding tissue.

Furthermore, because wear is significantly reduced, and because movement of the head relative to the shell is significantly reduced, materials may be selected without undue concern for their wear characteristics, such as the hard, brittle cobalt chromium and ceramic utilized in modern implants. Instead, far more durable materials, such as spring steel, may be selected to improve the fatigue life of the implant, and avoid fractures and failures that occur when brittle materials are used. Additionally, dissimilar metals need not be utilized, as in the cobalt chromium head and titanium neck that is popular in modern implants. Accordingly, galvanic corrosion is eliminated. In yet additional embodiments, composite materials, such as carbon fiber reinforced polymers may be suitable for use with the present invention as, due to the reduction in wear, materials need not be selected for their wear properties, be may instead be selected for strength, flexibility, or durability.

In at least one embodiment, the axle contains a lubricant reservoir, for retaining a predetermined amount of lubricant which may be selected to last for the life of the implant. In such an embodiment, the recess in the head and the axle are correspondingly dimensioned and configured such that lubricant may flow between the mating surfaces where the recess and axle rotate against one another. As such, the bearing created by the axle and the recess maintains constant lubrication. Additionally, debris may be carried back to the reservoir and maintained therein. In yet further embodiments, balls or rollers may be disposed between the axle and recess in order to further reduce friction and support radial loading. It will be appreciated that the term "axle" as used herein, refers to the structure which may be disposed interiorly of the head, and is not meant to connote any particular geometric limitation.

In yet another embodiment, the present invention reduces micro-motion and fatigue due to repeated stresses transferred through the implant from, e.g., walking, running, jumping, etc. In such an embodiment a cage is provided, which is to be fixed to the distal end of the neck of the present invention via a bushing. In a preferred embodiment, a suitable polymer with a damping quality is injection molded between the cage and the distal end of the neck, thereby securing the cage to the neck and forming the bushing. The cage may then be pressed or cemented inside the modular taper of the femur stem (which is inserted into a patient's femur) or the neck and cage may be implanted directly into the patient, as the case may be. In either embodiment, it will be appreciated that the cage will provide a rigid attachment point, while the bushing serves to at least partially isolate micro-motion, and other fatigue inducing stress, from the neck, thereby reducing fractures, corrosion, and eventual failure. Cementing the cage into the femur stem seals the majority of the bushing from the patient's tissue.

In at least one embodiment, the distal and proximal members are retained together via a shear interference fit of a retention member. Such a retention member should allow rotation of the distal member relative to the proximal member, but interfere with translational movement of the distal member relative to the proximal member. By way of non-limiting example a circular spring retention clip may be disposed about the axle and further in at least partially interfering relation with both the inner surface of the head and the outer surface of the axle. As such, rotation of the axle within the head is provided for, yet translation of the axle out of the head is prevented. By way of further example, a plurality of ball bearings may be utilized instead of a spring retention clip, which has the added benefit of reducing wear of the mating surfaces of the head and neck. In yet further examples, one or more dowel pins or set screws may be disposed through the head and into shear interfering relation with a channel disposed about the axle.

While the present invention has been described in the context of an orthopedic implant, and particularly intended for use as a human hip, the structure of the present invention is suitable for a variety of other uses, such as other human or animal joints, more specifically equestrian joints where excess weight is of concern, as well as robotic use, and commercial and industrial use, particularly in machinery that utilize joints with a primary direction of motion, but also require additional degrees of freedom.

Yet another embodiment of the invention provides a "sacrificial" or "galvanic" anode to shield critical components of the invention from corrosion. As described above, in the case of hip implants, the bending of the femur under load causes a voltage flow from a piezoelectric effect, which contributes to an electrical potential generated across various components of the implant. The triboelectric effect may also cause a buildup of charged particles due to the constant rubbing of the ball against a dissimilar liner.

Accordingly, such a sacrificial or galvanic anode may be selected from a material which is more anodic (i.e., having a greater electrochemical corrosion potential) than the materials selected for the remaining components of the hip implant itself. By way of non-limiting example, if an implant is made from steel or titanium, then a suitable anode may be comprised of zinc, aluminum, or magnesium. The anode is then placed in electrical communication with the implant itself, such that the implant does not corrode prior to the anode. However, releasing metallic ions and corrosion-related particles into the body is undesirable. In a preferred embodiment, the anode is sealed within an interior portion of the hip implant, such that corrosion-related particles do not escape the hip implant and are not released into the body. One such configuration is placing the anode within the aforementioned lubricant reservoir. Yet another embodiment may comprise fastening the anode to a distal end of the neck and/or axle of the present invention. When referring to neck of the present invention, distal refers to the end of the neck that is towards the head, while proximal refers to the end of the next that is towards the shank.

In yet another embodiment, honey, and most preferably bee honey, may be selected as a desirable lubricant for the inventive hip implant. Honey is a known preservative and this property is thought to be due to the presence of gluconic acid and hydrogen peroxide, both of which naturally occur in honey, and are responsible for the higher acid content and suppression of bacterial growth in honey. Another naturally occurring compound in honey, Methylglyoxal or "MGO" is thought to be the primary element contributing to the antibacterial properties of honey. Most types of honey include between 0-20 mg of MGO per kilogram of honey. Manuka honey, however, generally has at least 20 mg of MGO per kilogram of honey, but can include up to, and beyond, 800 mg of MG per kilogram of honey. Accordingly, Manuka honey is thought to be highly resistant to bacterial growth, has been shown to be effective at fighting infection within the body, and would be desirable in a most preferred embodiment of the present invention.

However, honey is also susceptible to crystallization and the likelihood of crystallization in honey is affected by the fructose to glucose ratio or "F/G ratio." Some research suggests that honey having an F/G ratio of less than 1.3 is likely to crystallize during long periods of storage, while ratios above are less likely to crystalize, and slower to crystalize if it does occur. It has also been found that Manuka honey made from Australian stingless bees generally has an F/G ratio of 1.4. Moreover, the melting point of crystallized honey tends to be between 104 and 122 degrees Farenheit. When honey is utilized as a lubricant in the present invention, it will circulate between the various moving parts of the invention (such as the axle, bearings, roller bearings, and inner surface of the head). Accordingly, any such crystallization would be worked and heated by the kneading and milling action between the various moving parts and will be amalgamated back into its liquid form.

Additionally, honey is an electrical conductor due to its electrolyte content in the form of various minerals and acids. Because of this conductivity, honey may act as an electrical conductor of the piezoelectric and triboelectric voltage generated outside the implant to a sacrificial anode installed inside of the device, thereby facilitating the corrosion resistance of such an embodiment. It is due to these qualities of honey, and others, that it is desirable as a life-long lubricant for the present invention. In a preferred embodiment, honey is injected in an amount and with pressure sufficient to fill the recess in the head to capacity, displacing all air from within the working bearing chamber.

Finally, the viscosity of honey does not preclude its use as a lubricant, as normal use of the prosthetic does not require large speed differentials between the various moving components of the hip implant. As such, significant shear forces within the honey, and therefore frictional losses due to "drag," are not anticipated.

Moreover, selection of a lubricant with a relatively high viscosity may provide an additional benefit. If a very low viscosity lubricant were utilized, frictional forces between the head and the axle may never be significant enough to cause the head to rotate within the acetabular region under no load. As such, the head would essentially be held captive by the relatively larger frictional forces between the head and the acetabular region, while the internal moving parts of the implant (such as the roller bearings and ball bearings) would constantly rock back and forth on essentially the same spot within the head, leading to accelerated wear within the head, including any bearings therein.

On the other hand, the viscosity of the lubricant may be selected such that the forces required to rotate the axle within the head are higher than the forces required to rotate the head within the acetabular region when the implant is not bearing the patient's weight. Accordingly, as the patient moves a leg forward (not under load) while walking or running, the head will tend to rotate within the acetabular region, while the axle will tend to be held captive within the head. At the same time, when the implant is bearing the patient's weight, frictional forces between the acetabular region and the head of the implant are increased, and careful selection of the lubricant's viscosity can result in an arrangement whereby the head is then held stationary within the acetabular region by the increased forces, while the axle rotates within the head to accommodate the patient's stride. Such an arrangement will result in a rotational migration of the head within the acetabular region akin to a ratcheting mechanism. As the patient strides forward with the implant unloaded, the head will rotate within the acetabular region. When weight is applied to the implant, frictional forces between the head and the acetabular region are increased, which tend to hold the head captive, while the axle is free to rotate within the head. In such an embodiment, a "new" or different portion of the head is presented within the acetabular region on each stride. As such, the internal moving parts of the implant (such as the roller bearings and ball bearings) are constantly introduced to a "new" or different portion of the inner surface of the head as well, which spreads mechanical wear out over the entire surface of the implant.

In a typical prior art hip implant, the head of a hip implant does not rotate independently of the neck portion and spans approximately 58 degrees of contact within an acetabular region or cup. As such, only about one sixth of the surface area of the head is utilized as a "wear surface." The present invention permits the entire 360-degree span of the head to be utilized as a wear surface due to the independent rotation of the head and neck. Accordingly, mechanical wear of the present invention can be reduced by at least a factor of six relative to prior art hip implants due to selection of a lubricant having sufficient viscosity. Other features of the present invention further reduce wear and enhance the service life of the inventive hip implant.

In additional embodiments, the viscosity of the lubricant may be selected to achieve different rotational characteristics. While relatively high viscosities will produce substantially unidirectional movement of the head within the acetabular region, lower viscosities may produce bidirectional movement of the head within the acetabular region, as may be desired.

In yet another embodiment of the present invention, it may be desirable to provide a seal made from natural fibers and/or animal hide, such as leather, in place of a synthetic seal. Synthetic seals, such as those made from butyl and silicone, tend to form a smooth, glossy skin on the outer surface of the seal. Seals which are to be used in relatively high pressure applications require a harder material and high machine tolerance, while softer seals are more compliant to varying dimensional changes. Over time, synthetic seals, especially those made from injection molding processes, will wear at the point(s) of contact, eventually breaking the skin and disintegrating over time. The polymers that make up synthetic materials also tend age over time and become brittle leading to yet another mode of failure.

On the other hand, leather is highly resistant to wear and tearing, has a relatively low coefficient friction, and is non-abrasive. Accordingly, when disposed against moving parts, leather can be expected to maintain a long working lifespan. Additionally, leather generally contains small surface wells that can be impregnated with different materials, such as lubricant(s) including honey. A single leather seal can last beyond the service life of a typical hip implant, especially if kept wet. Yet another benefit of leather is that once wet, it tends to swell. Accordingly, if sized appropriately, an initially dry leather seal can swell to tolerance if placed in a wet environment. Furthermore, in certain embodiments of the invention, any lubricant placed in the reservoir will displace all air in the reservoir, and thus create a slight vacuum when the unit is sealed. Accordingly, such a leather seal need only form a barrier of separation between the lubricant and the body in which the implant is disposed. It is for these reasons that a preferred embodiment of the present invention utilizes a seal or gasket made of leather, and not from synthetic materials.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 7 is a section view taken along line 7-7 of FIG. 6.

FIG. 8 is a perspective view of a distal member according to one embodiment of the present invention.

Like reference numerals refer to like parts throughout the several views of the drawings.

DETAILED DESCRIPTION OF THE PREFERRED EMBODIMENT

Figure 1:
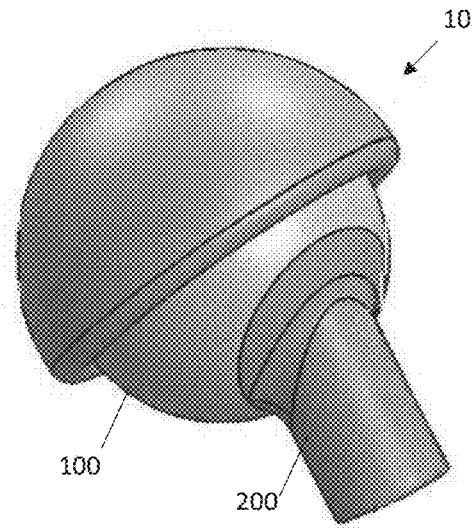
FIG. 1 is a perspective view of an orthopedic hip prosthesis in accordance with one embodiment of the present invention.
Figure 3:
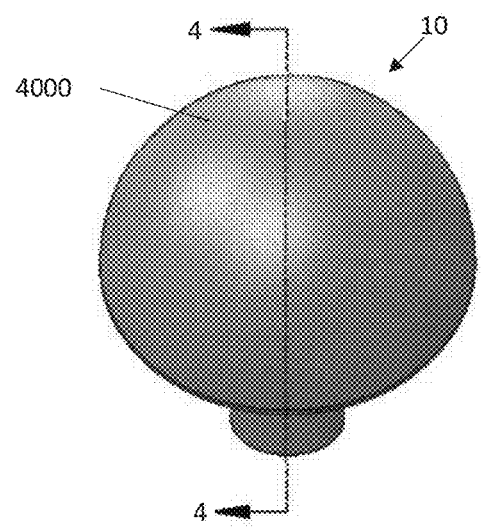
FIG. 3 is a perspective view of an orthopedic hip prosthesis in accordance with one embodiment of the present invention.
Figure 2:
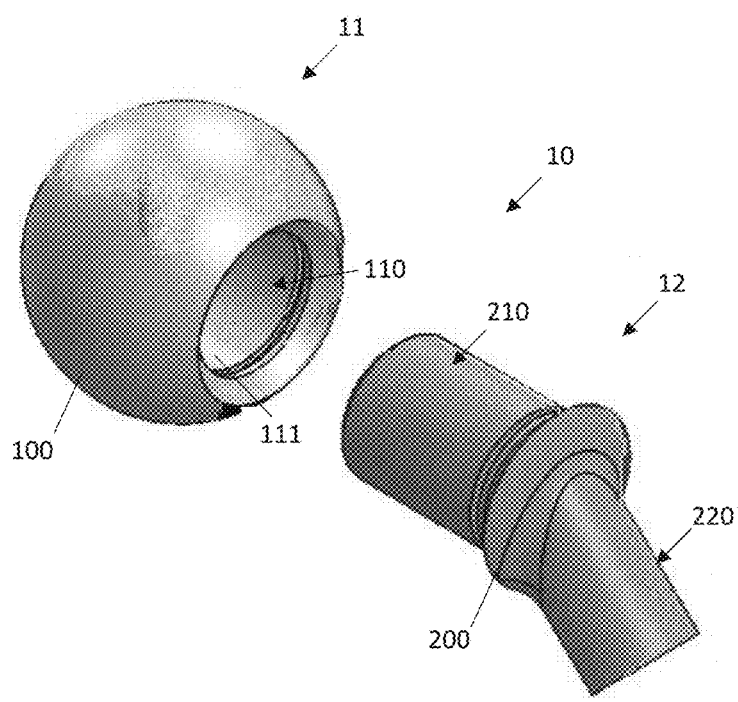
FIG. 2 is an exploded perspective view of an orthopedic hip prosthesis in accordance with one embodiment of the present invention.

With reference to FIGS. 1-4, one embodiment of the present invention is directed to an orthopedic hip prosthesis 10 including a proximal member 11 and a distal member 12, as best shown in FIG. 2. The head 100 is a substantially spherical member, which approximates the geometry of a traditional hip replacement prosthesis with notable exceptions. The head 100 will be generally of a larger diameter than its modern equivalents due to the elimination of the "traditional" liner, which tends to be quite thick in dimension, and shell (or, in certain embodiments, replacement of the "traditional" liner and shell with at least a thin shell). Additionally, the head 100 includes a recess 110, such as shown in FIG. 2, with the recess 110 having an inner surface 111.

Figure 4:
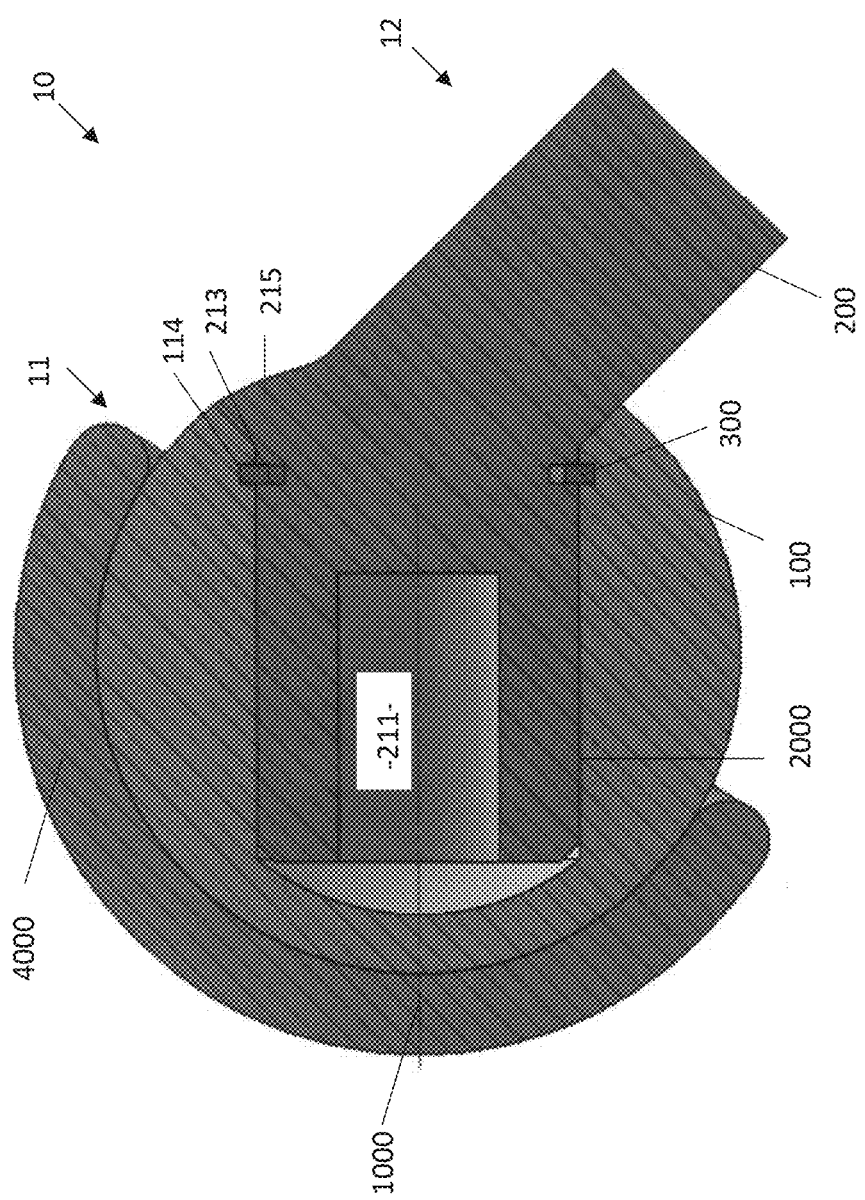
FIG. 4 is a section view taken along line 4-4 of FIG. 3.
Figure 6:
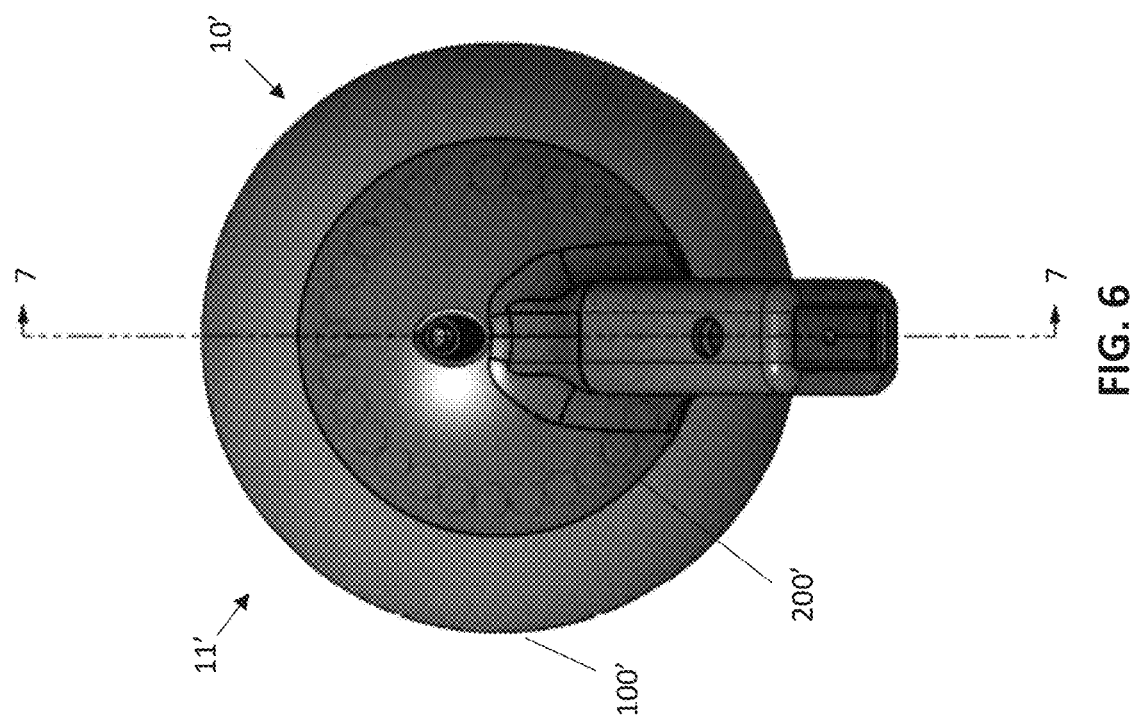
FIG. 6 is a rear perspective view of the orthopedic hip prosthesis depicted in FIG. 5.
Figure 5:
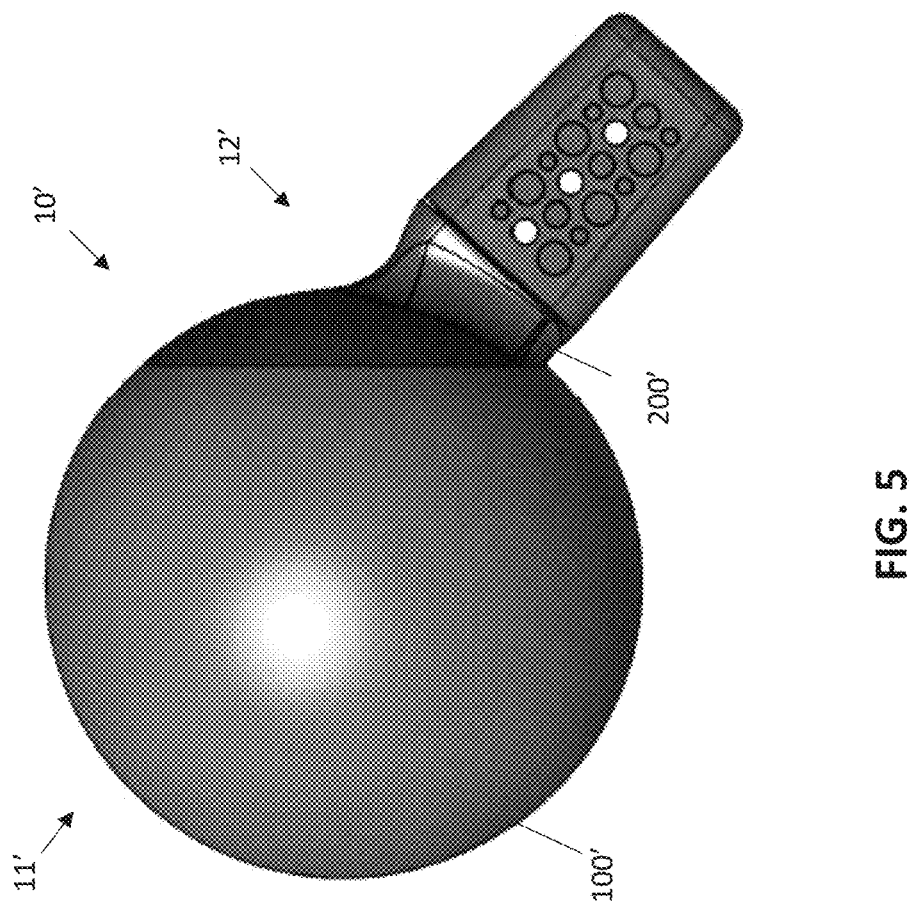
FIG. 5 is a side perspective view of an orthopedic hip prosthesis in accordance with another embodiment of the present invention.

Another component of the orthopedic hip prosthesis 10 is the neck 200. The neck 200 of the depicted embodiment includes an axle 210, as shown in FIG. 2, which has an outer surface 214. As may be seen, the axle 210 is correspondingly dimensioned and configured with the recess 110 to be inserted therein, with the outer surface 214 and inner surface 111 defining a mating interface 2000 between the head 100 and the neck 200, as best shown in FIG. 4. The neck 200 may also include a shank 220, shown in FIG. 2, which may be either implanted directly into the patient's femur, supplanting the need for a traditional femur stem, or combined with a traditional femur stem, either integrally or modularly.

In certain embodiments, and with reference to FIG. 4, the neck 200 may also include a contour 215 (or 215' as depicted in later Figures) disposed between the axle 210 and shank 220. The contour 215 may be dimensioned and configured to provide a substantially flush mount between the neck 200 and head 100. The contour 215 may also be geometrically configured to facilitate a substantially smooth transition from head 100 to neck 200, e.g., in the scenario of extreme lateral movement of the patient (such as raising one's leg sideways) where the neck 200 may otherwise impinge on the thin shell 4000 (if used) or other structure, such as the acetabular region of the pelvis. It will be appreciated that the thin shell 4000 depicted in the Figures is presented for purposes of facilitating the structure and operation of the present invention, and that a thin shell 4000 utilized in conjunction with the present invention need not conform to the particular structure or dimensions thereof.

Certain embodiments of the neck 200 and head 100 may also include a reservoir 211, as shown in FIG. 4, which may be formed by providing one or more recesses and/or reliefs within the head 100 and neck 200, such that a reservoir 211 for lubricant is created and sufficient room is provided for the lubricant to flow to and from the mating interface 2000. In one embodiment, the lubricant may be comprised of human or animal tallow, which, depending upon its various characteristics, may be solid at room temperature, but have a melting point below or near 98 degrees Fahrenheit, which in turn, makes it suitable for packing the reservoir at room temperature, yet facilitating a lubricant bath within the head 100 once warmed by the patient's body. Alternatively, vitamin E, hydrolyzed collagen gelatin, or a dry lubricant can be used. As may be appreciated, the lubricant should be selected such that, if a leak occurs, the patient's tissue will not be negatively impacted. Additionally, the reservoir, and other negative space within the prosthesis 10, should be packed until no air remains in order to further reduce the likelihood of leaks. In some embodiments the reservoir 211 may be packed manually. Additionally, as is depicted in alternative embodiments herein, a lubricant channel may be provided such that the reservoir may be packed from the exterior of the head 100, e.g., by using a syringe to force lubricant into the reservoir 211 and other negative space, thereby eliminating any air pockets. Specifically, if no air remains in the negative spaces, suction would hold the viscous lubricant within the prosthesis 10.

In yet further embodiments, the neck 200 is rotationally secured within the head 100 via a spring retention clip 300. In the depicted embodiment, both the head 100 and neck 200 have correspondingly dimensioned and disposed retention clip channels 213, 114 (as best depicted in FIG. 4). The retention clip 300 will be preselected such that it may be compressed about the axle 210 when the neck 200 is installed within the recess 110. When the retention clip 300 is moved into alignment with the retention clip channel 114 in the head, the retention clip 300 will expand at least partially into the channel 114, thereby fixing the neck 200 within the head 100, yet allowing the neck 200 to rotate about its axis of rotation 1000.

With reference now to FIGS. 5-8, a rotationally free, but translationally secure mounting of the neck 200' within the head 100' is accomplished via a plurality of ball bearings disposed about the neck 200' in at least partially shear-interfering relation with the neck 200' and head 100'. More specifically, the head 100' and neck 200' are mated so as to rotate relative to one another, but are constrained from translational movement. As can be seen, the plurality of ball bearings facilitate such rotational movement of the neck 200' within the head 100', but substantially preclude translational movement of the neck 200' relative to the head 100', due to the interference created by the plurality of ball bearings. With reference to FIG. 7, the retention channel 213' is at least partially disposed within the head 100' and at least partially disposed within the neck 200'. As such, when one or more ball bearings are disposed within the retention channel 213, translational movement of the head 100' relative to the neck 200' is precluded via the shear-interfering relation of the ball bearings within the retention channel 213.

In order to facilitate assembly of the present invention, a bearing passage 240' (see FIG. 7) may be provided which is in communication with both the retention channel 213 as well as the exterior of the neck 200'. Once the neck 200' is inserted within the head 100', the plurality of ball bearings 600 may be inserted into the bearing passage 240 and allowed to travel into and around the retention channel 213'. Once the retention channel 213' is packed with ball bearings 600, a plug 240 and/or set screw 242 is inserted to maintain the ball bearings 600 within the retention channel 213'.

As can also be seen with reference to FIG. 7, a lubricant channel 230 is provided which facilitates communication of the reservoir 211' with the exterior of the assembly. In such an embodiment, the lubricant may be introduced via the channel and allowed to overflow the channel, backfilling the regions around the rollers 400 and ball bearings 600 until no air is present within such regions. A gasket 213 may be provided to prevent the lubricant from traveling any further, and the plug 240 and/or set screw 242 precludes the lubricant from traveling back out of the lubricant channel 230.

Additionally, and as best shown in FIG. 8, the distal member 12' includes a neck 200' which provides for the use of rollers 400. Though only a certain number of rollers are depicted, it will be appreciated that as many as desired may be utilized, the limiting factors being the diameter of the rollers and the circumference of the axle 210'. In order to accommodate rollers 400, a relief 218 is provided within the axle 210, but it will be appreciated that other configurations may provide equivalent functionality.

As can also be seen in FIGS. 7 and 8, some embodiments of the invention may have an additional component, namely a cage 500 is provided to be mounted to the end of a shank 220'. The cage 500 may be mounted to the shank 220' via a suitable, non-rigid adhesive. In a preferred embodiment, the cage 500 is held in spaced relation to the shank 220' and then a non-rigid polymer, such as polyurethane, is injection molded through the sprue passages 511 and allowed to flow between the neck 200' and cage 500', and out of the apertures 510, thereby forming a bushing. In this regard, a stable but flexible connection is formed between the cage 500 and the neck 200'. As such, stresses transferred through a femur shank to the neck 200' are absorbed by the dampening quality of the polymer bushing disposed between the cage 500 and neck 200'.

Figure 9:
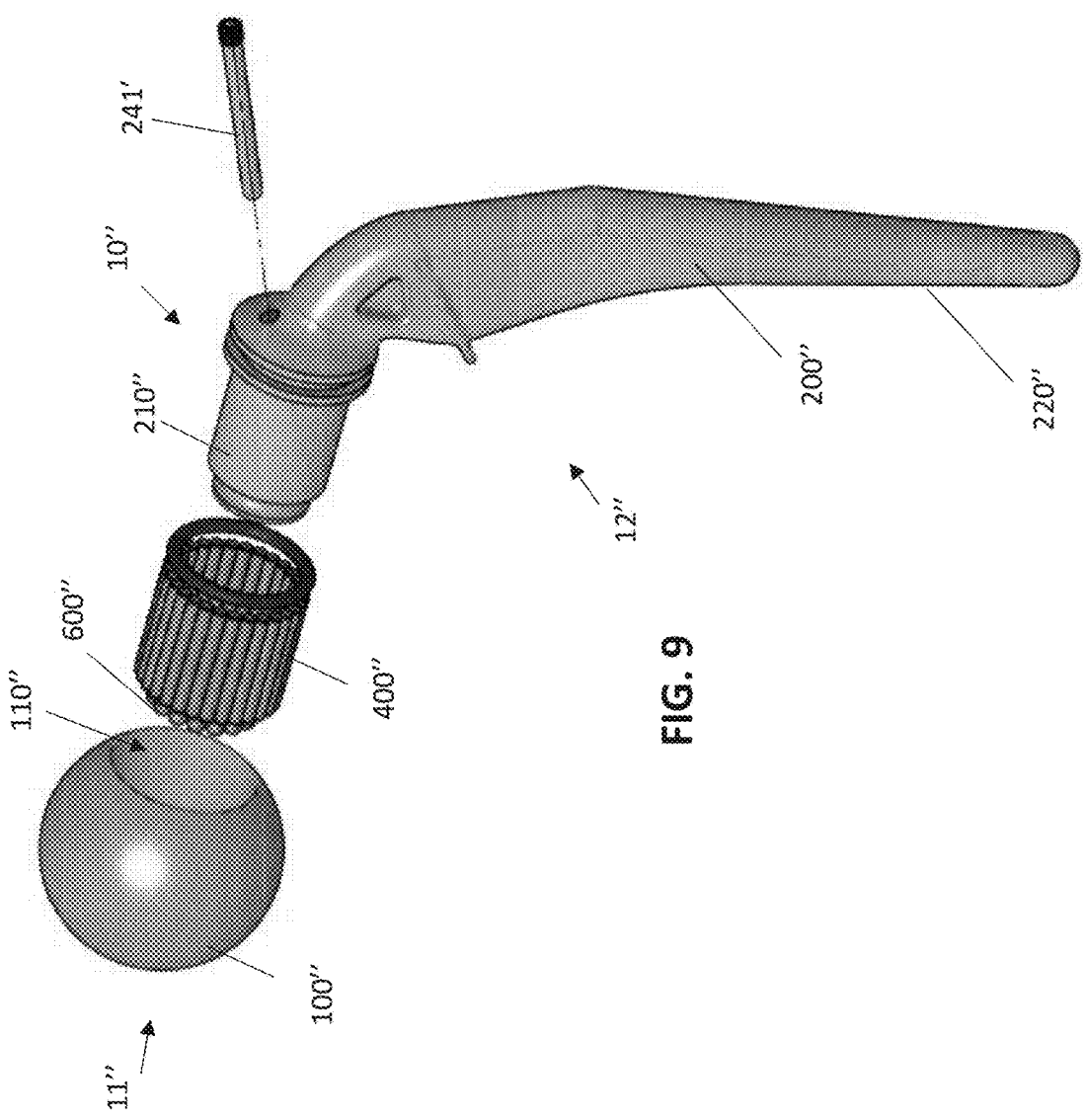
FIG. 9 is an exploded perspective view of an orthopedic hip prosthesis according to yet another embodiment of the present invention.
Figure 10:
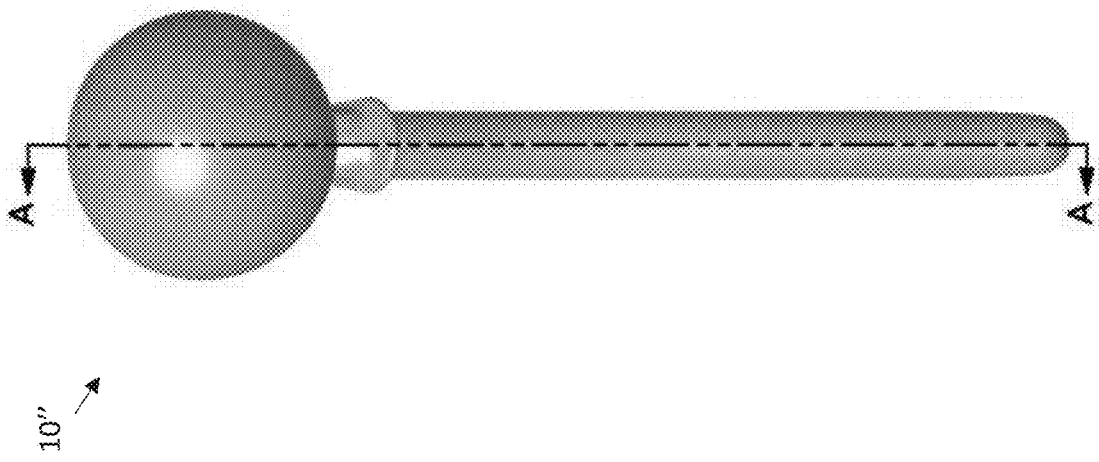
FIG. 10 is a front plan view of the orthopedic hip prosthesis depicted in FIG. 9
Figure 11:
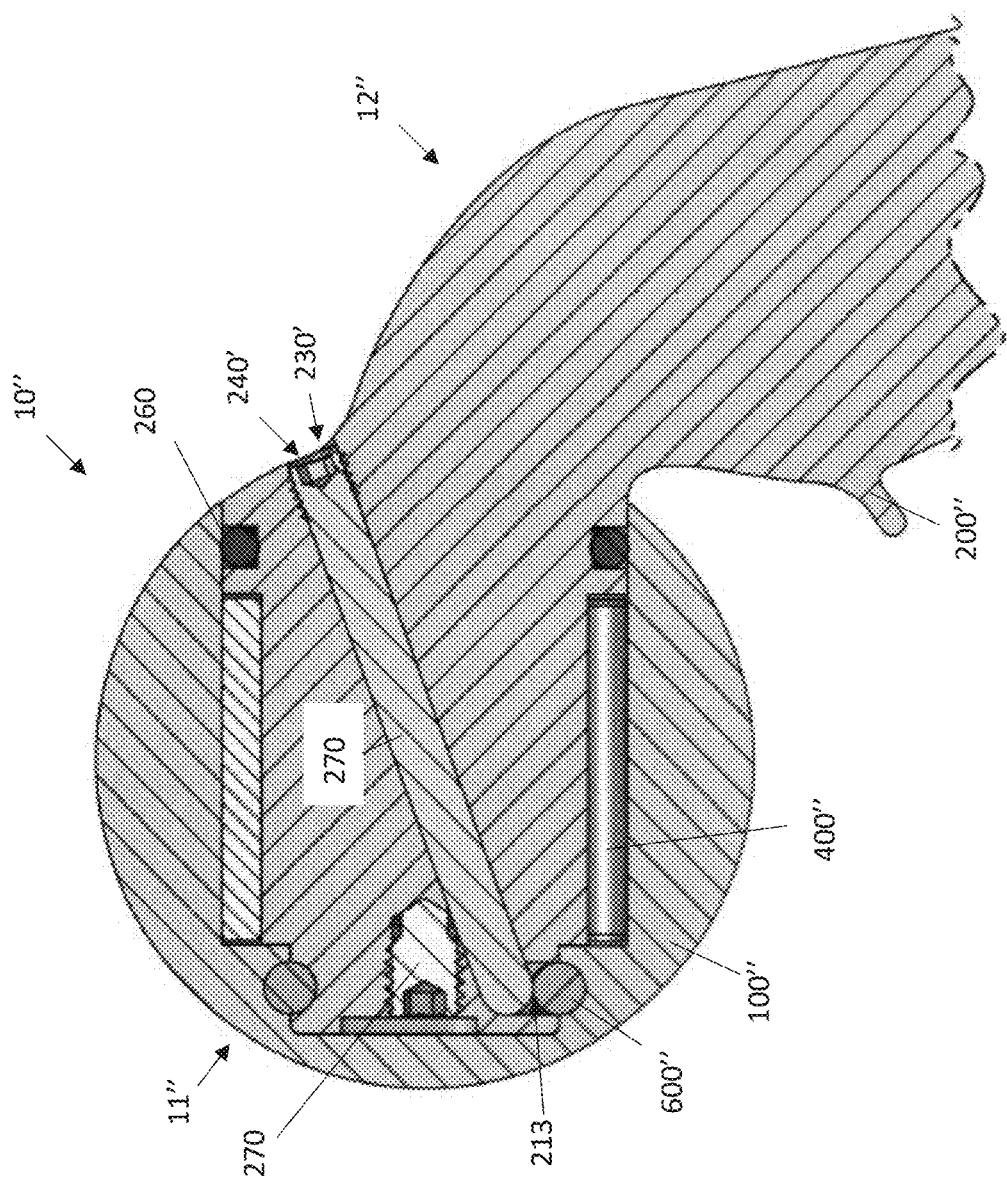
FIG. 11 is a partial section view taken along line A-A of FIG. 10.

Turning now to FIGS. 9-11, yet another embodiment of an orthopedic hip prosthesis 10" is disclosed. According to the disclosed embodiment, the invention includes a proximal member 11" including a head 100", as well as a distal member 12" including a neck 200". The plurality of the ball bearings 600" and retention channel 213' are disposed on a proximal end of the neck (closer to the head 100"), such that they are disposed further within the recess 110" of the head 100" relative to previously disclosed embodiments. Such an arrangement provides more room for rollers 400" and/or a seal 260".

Additionally, as can be seen in FIG. 11, the bearing passage 240" and lubricant channel 230" may be combined into a single structure, which extends from a distal side of the neck 200" (i.e., further away from the head 100") to the retention channel 213' itself. Such an arrangement facilitates assembly of the present invention. In particular, the neck 200" may be inserted into the recess 110" of the head 100", and then a plurality of ball bearings 600" can be inserted into the bearing passage 240" and allowed to settle within and around the retention channel 213'. Because the retention channel 213' includes corresponding structure on both the neck 200" and the inner surface 111" of the head 100", the bearings will then perform a "locking" function, as any attempt to remove the neck 200" from the head 100" after insertion of the bearings 600" will cause the bearings 600" to interfere against the retention channel 213' in what has been previously described as a shear-interfering relationship.

Once the plurality of bearings 600" are inserted, a lubricant may be injected via the lubricant channel 230' with sufficient volume and pressure to cause the lubricant to fill the lubricant channel 230', the retention channel 213', any reservoirs within the neck 200", the various interstices between bearings 600" and rollers 400', and force any remaining air out past the seal 260. Once a suitable plug 241' is inserted, the entire recess 110" within the head 100" is then completely evacuated of air, and a slight vacuum is created, particularly if the head 100" attempts to separate from the neck 200", which is beneficial to trapping lubricant (and any particulate matter) within the recess 110" itself. As described above, such a lubricant may comprise a naturally occurring, bio-compatible fluid such as honey, bee honey, and most preferably, Manuka bee honey.

The present invention also makes use of a seal 260, which in a preferred embodiment may be made of a naturally occurring, suitably durable fiber such as leather. The seal is disposed in an annular channel running circumferentially about the axle 210". As disclosed above, if a liquid lubricant is utilized, the leather may absorb some of the liquid and swell to tolerance. Accordingly, when first packing the device with ball bearings 600" and lubricant, the device may leak until the seal 260 is able to sufficiently swell and form a liquid barrier.

With specific reference to FIG. 11, an anode 270 is also fastened to a distal end of the neck 200". In the depicted embodiment, the anode 270 comprises a threaded fastener to facilitate sufficient contact with the neck 200". In a most preferred embodiment, the anode 270 may be comprised of aluminum, magnesium, or zinc. As can be seen, fastening the anode 270 to a distal end of the neck 200" results in disposition of the anode deep within the recess 110" of the head 100". As such, metallic ions and other particles released from the anode 270 as it corrodes sacrificially are trapped within the recess 110". Due to the slight vacuum created when lubricant is introduced in a most preferred embodiment, any such metallic ions and other particles will tend to stay within the recess 110" and will not be motivated to travel outside of the prosthesis 10" itself.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An orthopedic hip prosthesis comprising:
   a prosthetic femoral neck sized and configured to be fixedly connected to a femur of a patient, the prosthetic femoral neck including a cylindrical axle extending from a proximal end and a femoral shank extending from a distal end, said axle defining an outer circumferential surface;
   a prosthetic femoral head configured to be rotationally connected to said prosthetic femoral neck, said prosthetic femoral head comprising a cylindrical recess defining an inner circumferential surface, wherein the axle of the prosthetic femoral neck is rotationally engaged within the recess of the prosthetic femoral head;
   a plurality of ball bearings positioned on a proximal end of the neck between said outer circumferential surface of said axle and said inner circumferential surface of said recess, said plurality of ball bearings disposed to restrict translational movement of said prosthetic femoral neck relative to said prosthetic femoral head, said plurality of ball bearings being retained inside an annular retention channel;
   a plurality of roller bearings positioned between said outer circumferential surface of the axle and said inner circumferential surface of the recess, the plurality of roller bearings disposed to support rotational movement between the prosthetic femoral head and the prosthetic femoral neck; and
   a naturally occurring, bio-compatible lubricant disposed within said orthopedic hip prosthesis between said cylindrical recess and said cylindrical axle, wherein said naturally occurring, bio-compatible lubricant comprises bee honey,
   wherein said annular retention channel is disposed proximally of said plurality of roller bearings on said neck,
   wherein said prosthetic femoral head and said prosthetic femoral neck are configured to accommodate coaxial motion of a hip joint.

2. An orthopedic hip prosthesis as recited in claim 1 further comprising a bearing passage, said bearing passage in communication with said annular retention channel at one end.

3. An orthopedic hip prosthesis as recited in claim 2 wherein the other end of said bearing passage is disposed in communication with a distal side of said neck.

4. An orthopedic hip prosthesis as recited in claim 1 further comprising a seal disposed circumferentially about said neck, distally of said plurality of roller bearings on said neck.

5. An orthopedic hip prosthesis as recited in claim 4 wherein said seal is comprised of naturally occurring fibers.

6. An orthopedic hip prosthesis as recited in claim 5 wherein said seal swells to tolerance when wet.

7. An orthopedic hip prosthesis as recited in claim 5 wherein said seal is comprised of leather.

8. An orthopedic hip prosthesis as recited in claim 1 further comprising a sacrificial anode disposed in communication with at least one of said neck and said head.

9. An orthopedic hip prosthesis as recited in claim 1 further comprising an aluminum fastener disposed within the neck on a proximal end thereof.

10. An orthopedic hip prosthesis as recited in claim 1 wherein said honey comprises Manuka honey.

11. An orthopedic hip prosthesis as recited in claim 1 wherein said honey contains at least 20 milligrams of methylglyoxal per kilogram of said honey.

* * * * *